United States Patent [19]
Baik et al.

[11] Patent Number: 5,980,870
[45] Date of Patent: Nov. 9, 1999

[54] HERB MEDICINE EXTRACT-CONTAINING NON-BLEEDING STRIPED DENTIFRICE COMPOSITION

[75] Inventors: In Sub Baik; Jong Gi Lee, both of Taejon; In Sik Cho, Seoul; Youn Woo Park, Taejon-shi, all of Rep. of Korea

[73] Assignee: Aekyung Industrial Co., Ltd., Seoul, Rep. of Korea

[21] Appl. No.: 08/934,544

[22] Filed: Sep. 19, 1997

Related U.S. Application Data

[63] Continuation of application No. 08/507,706, Jul. 26, 1995, abandoned.

[30] Foreign Application Priority Data

Jul. 26, 1994 [KR] Rep. of Korea ....................... 94-18058

[51] Int. Cl.$^6$ ........................................ A61K 9/16
[52] U.S. Cl. ................................ 424/58; 424/49
[58] Field of Search ......................... 424/49–58

[56] References Cited

U.S. PATENT DOCUMENTS

| | | |
|---|---|---|
| 3,928,559 | 12/1975 | Patino et al. . |
| 3,980,767 | 9/1976 | Chown et al. . |
| 4,007,259 | 2/1977 | Patino et al. . |
| 4,069,311 | 1/1978 | Mannara . |
| 4,358,437 | 11/1982 | Duke . |
| 4,456,585 | 6/1984 | Hayes et al. . |
| 4,487,757 | 12/1984 | Kiozpeoplou . |
| 4,518,578 | 5/1985 | Hayes et al. . |
| 4,568,534 | 2/1986 | Stier et al. . |

FOREIGN PATENT DOCUMENTS

| | | |
|---|---|---|
| 0 331 617 A1 | 9/1989 | European Pat. Off. . |
| 56-083416 | 7/1981 | Japan . |
| 57-056415 | 4/1982 | Japan . |
| 57-058610 | 4/1982 | Japan . |
| 57-058611 | 4/1982 | Japan . |
| 57-058613 | 4/1982 | Japan . |
| 59-013712 | 1/1984 | Japan . |
| 59-016814 | 1/1984 | Japan . |
| 5-152313 | 8/1984 | Japan . |
| 62-058329 | 12/1987 | Japan . |
| 01-151512 | 6/1989 | Japan . |
| 56-83416 | 7/1981 | Rep. of Korea . |
| 57-56415 | 4/1982 | Rep. of Korea . |
| 57-58610 | 4/1982 | Rep. of Korea . |
| 57-58611 | 4/1982 | Rep. of Korea . |
| 57-58612 | 4/1982 | Rep. of Korea . |
| 57-58613 | 4/1982 | Rep. of Korea . |
| 5-152313 | 8/1984 | Rep. of Korea . |
| 2-17524 | 4/1990 | Rep. of Korea . |
| 91-1919 | 3/1991 | Rep. of Korea . |
| 91-01919 | 3/1991 | Rep. of Korea . |
| 3-32524 | 5/1991 | Rep. of Korea . |
| 3-66283 | 10/1991 | Rep. of Korea . |
| 91-18007 | 1/1993 | Rep. of Korea . |
| 94-25562 | 12/1994 | Rep. of Korea . |

OTHER PUBLICATIONS

Korean Pat Publication No. 91–1919, 1991.
Japanese Pat. Publication Laid–Open Nos Sho 56–83416, Sho 57–58610, 1982.
Sho 57–58611 Sho 57–58612 Sho 57–58513 Sho 57–56413, 1982.
Sho 59–152312 Hei 1–151512 Jap. Pat Pub. Hei 3–66283 Hei 3–32524,1985.
Derwent Lion Corp JP 57082307, May 1982.
Derwent Hasegawa JP 54096532, Jul. 71979.
Derwent Taito JP 51006230, Jan. 1976.
Derwent Lion Dewtifrics JP 39017166, 1968.
GA. 121: 42453 WU CN 1078882, Dec. 1993.
GA. 117: 169886 Ajinomoto JPN 041730700, Jun. 1992 (+Derwent), Jun. 1992.
Ga. 104: 10428 Kawai JPN 60163810, Aug. 1985 (+Derwent).
Derwent Sunstar JP 06025000, Feb. 1994.
Derwent Lion Corp JP 58134012, Aug. 1983.
Derwent Rohto Pharm JP 58121218, Jul. 1983.
Derwent Tsurui Yakuhin Kogy JP 58057320, Apr. 1983.
Derwent Tsurui Yauhin Kogy JP 57085319, May 1982.
Natural Color Guide Warner Jenkinson Company The Natural Resource, Mar. 1993.
Massa and Miniati Antho Cyanins in Fruits Vegetables and Grains pp. 1–25, 283–288 CRC Press, 1993.
Perry et al Medicinal Plants of East and Southeast Asia Mit Press Cambridge, Mass Lib. of Congress –RS 164, p. 47 *Taraxacum Platycarpum.* p. 99, *Gardenia Jasminoides* pp. 349–350, *Lonicera Japoonica.* p. 71, *Scutellaris Bricalensis.* p. 194, *Pulsatilla.* pp. 102, 333–334, *Pueraria Thumbargiana*, pp. 224–225.

*Primary Examiner*—Shep K. Rose
*Attorney, Agent, or Firm*—Merchant, Gould, Smith, Edell, Welter & Schmidt

[57] ABSTRACT

A herb medicine extract-containing non-bleeding striped dentifrice composition, consisting essentially of a striped dentifrice component and a base dentifrice component, each component comprising the following ingredients at the substantially same amount: a. an abrasive that has a BET surface area of 10 m$^2$/g or less and an average particle diameter of 1 to 30 μm upon measurement by Coulter Counter method, and shows oil absorption (linseed oil, ml/100 g) of 50 or less; b. a binder selected from the group consisting of xanthan gum, carrageenan, sodium carboxymethylcellulose, and the mixtures thereof; c. an alkyl sulfonate of anionic surfactants; and d. a humectant, and said striped dentifrice component containing herb medicine extracts at an amount of 0.001 to 10% by weight, on the basis of dry solid substance. It is non-bleeding by virtue of the substantially same formulation in the two components and the herb medicine extracts allow the dentifrice composition to suppress the formation of plaque.

5 Claims, No Drawings

HERB MEDICINE EXTRACT-CONTAINING NON-BLEEDING STRIPED DENTIFRICE COMPOSITION

This is a Continuation of application Ser. No. 08/507,706, filed Jul. 26, 1995 now abandoned.

BACKGROUND OF THE INVENTION

1. Field of the invention

The present invention relates, in general, to a herb medicine extract-containing non-bleeding striped toothpaste and, more particularly, to a herb medicine extract-containing striped dentifrice composition which exhibits no bleeding of colorant from one component into the other and suppresses the formation of plaque.

2. Description of the Prior Art

Various prior techniques for striped dentifrice products containing, for example, water soluble dyes are known, including U.S. Pat. Nos. 4,358,437, 4,569,534 and 4,487,757. U.S. Pat. No. 4,358,437 discloses a striped toothpaste which comprises a transparent gel base and an opaque paste stripe containing calcium carbonate abrasive and metasilicate ingredient. U.S. Pat. No. 4,568,534 discloses a striped dentifrice comprising an aqueous striping composition containing a pH sensitive dye and a gelling agent mixture of sodium carboxymethyl cellulose and calcium carrageenan, and a white anhydrous toothpaste formulation. U.S. Pat. No. 4,487,757 suggests a striped toothpaste extruded from a tube comprising two separate portions one of which contains sodium bicarbonate particles stabilized by a compatible water insoluble polishing agent such as calcium carbonate, the other portion being in an acid pH and containing an acid and 0.001 to 0.1% of a coloring agent which is a 1% aqueous dye solution.

However, the water-soluble dyes contained in the toothpastes of the above-cited patents are more likely to be bled or leak from the colored dentifrice stripe into the toothpaste base if the toothpastes are stored at high temperatures for a long time, thereby degrading the quality of article.

To avoid this problem, use of synthetic pigments such as phthalocyanine in a colored dentifrice stripe has been proposed as disclosed in U.S. Pat. Nos. 4,456,585 and 4,518,578. These synthetic phthalocyanine pigments, however, are not allowed for use in dentifrices in many countries because they may be harmful to human body. Therefore, alternative non-bleeding colorant and/or formulation is needed.

U.S. Pat. Nos. 3,928,559 and 4,007,259 disclose speckled dentifrices wherein the speckles contain a colorant blended with the water insoluble thermoplastic polymer particles such as polyethylene, said colorant being a pigment such as ultramarine blue, ferric oxide, metallic lakes and the like, with the aim of preventing the bleeding of coloring materials. U.S. Pat. Nos. 4,069,311 and 4,069,312 also disclose striped dentifrices wherein said stripes are thermoplastic binder material containing colorants including any physiologically acceptable dye or pigment such as inorganic pigments, organic dyes, metallic lakes thereof, chlorophyll and carotene.

U.S. Pat. No. 3,980,767 discloses a striped toothpaste consisting of a main transparent gel body free of dental abrasive and containing humectant, thickening agent such as cellulose esters or carrageenan: and a secondary gel body containing a dental abrasive, humectants, thickening agent, detergent and optionally an insoluble coloring material in the form of a contrasting stripe within the main gel body.

European Pat. Publication No. 0 331 617 A1 discloses a striped dentifrice consisting essentially of a combination of two dentifrice components: one translucent gel colored dentifrice component comprising an organic pigment, such as β-carotene or chlorophyll, and xanthan gum as the sole gelling agent, and an opaque white paste dentifrice component composing a cellulase resistant gelling agent, such as a kappa carrageenan mixture, in a liquid vehicle containing different dentally acceptable polishing agents.

The prior art non-bleeding striped toothpastes, however, are in difficulty in showing clear stripe and appropriately distributing the different dentifrice components in squeezing the toothpaste tubes because the striping portion and the base portion are different from each other in flowing property, which is attributable to the difference in formulation therebetween.

The prior art also discloses dentifrices containing herb medicine extracts known to be suppressive of the formation of plaque, as disclosed in Korean Pat. Appln. No. 93-9048 to the present applicant, Korean Pat. Publication No. 91-1919, Korean Pat. Publication Laid-Open No. 91-18007, Japanese Pat. Publication Laid-Open Nos. Sho 56-83415, Sho 57-58610, Sho 57-58611, Sho 57-58612, Sho 57-58513, Sho 57-56415, Sho 59-152313 and Hei 1-151512, and Japanese Pat. Publication Nos. Hei 3-66283 and Hei 3-32524. Most of the herb medicine extracts described in the above-cited patents contain considerable amounts of coloring materials in addition to pigments. When these herb medicine extracts are used for striped toothpastes, the bleeding of the coloring materials or pigments readily occurs in the existing toothpaste formulations. The colorants can be laboratorially separated from herbs, which, however, costs too much, making it difficult to apply the herb extracts in commercial practice. In addition, useful ingredients which suppress the formation of plaque and may also be removed when separating the colorants. Owing to these reasons, the use of such herb extracts in striped dentifrices has not been reported, thus far.

In particular, Korean Pat. Appln. No. 93-9048 discloses an invention that relates to products for oral cavities, such as plaque formation inhibiting toothpaste, mouthwash, chewing gum, and gingival massage cream. More specifically, selected plaque formation inhibiting ingredients includes Taraxacum extract or, other than Taraxacum extract, Lonicera flower extract, Scutellaria root extract, Gardenia fruit extract, Pulsatilla root extract, Pueraria root extract or plant extract selected from the combination of two or more of those.

This reference teaches that it is known that primary diseases developed in teeth or areas around teeth are tooth decay and periodontal disease, and the main cause of such disease is dental plaque, and that extracts of plants of various species have been used to solve these problems. Experiments are disclosed on the antibiotic property and plaque formation inhibiting ability of extracts from many different species of plants that have been publicized or not publicized in prior arts of the present field and other related reference for long period of time. It was found that extract from Taraxacum whose uses were not known in the disclosed field inhibits the growth of and disinfects streptococcus mutants, and therefore, prevents the formation of plaque and better effect is shown when Taraxacum extract is combined with other certain plant extracts.

Korean Pat. Appln. No. 93-9048 thus discloses a composition for oral cavity that includes Taraxacum extract as plaque formation inhibiting ingredient. Furthermore, the reference discloses a composition for oral cavity that includes, other than Taraxacum extract, Lonicera flower extract, Scutellaria root extract, Gardenia fruit extract, Pulsatilla root extract, Pueraria root extract or plant extract selected from the combination of two or more of those.

Plant extracts are also disclosed that are obtained from the following plants: Taraxacum used is the whole plant body of Taraxacum platycarpum H, Dahlstedt or Carduaceae, and has antibiotic and anti-Eumycetes effect, therefore, it is used in eastern medicine for many kinds of inflammation; Lonicera flower used is the flower of Lonicera japonica Thunberg, and has antibiotic, antivirus, anti-Eumycetes and astringent effect, therefore, it is used in eastern medicine for inflammation in mouth, bleeding caused by inflammation, and swelling and used as general inflammation medicine when combined with Taraxacum; Scutellarai root is peeled root of *Scutellaria baicalensis* Georgi and has antibiotic, antivirus, anti-Eumycetes and sedative effect, therefore, it is used in eastern medicine for inflammation, tooth ache, oral cavity ache, tooth decay, and periodontitis by combining with Gardenia and etc.; Gardenia fruit used is a fruit of *Gardenia jasminoides* Ellis tree or Rubia Akane and has stopping of bleeding, antibiotic and sedative effect, therefore it is used in eastern medicine for many kinds of inflammation including inflammation inside a mouth and bleeding caused by inflammation; Pulsatilla root used is a root of *Pulsatilla koreana* Nakai or Carduaceae and has antibiotic, anti-Eumycetes and astringent effect, therefore, it is used in eastern medicine for tooth ache and many kinds of inflammation; and Pueraria root is a peeled root of *Pueraria thunbergiana* Bentham and has pain-alleviating and anti-inflammation effect, therefore, it is used in eastern medicine for tooth ache and inflammation inside of mouth by combining with Scutellaria root and etc.

These extracts of medicine plants are disclosed as being produced by the disclosed method, and it is disclosed that it is preferred that volatile solvents such as ethanol and methanol of the amount 10 times as large as the amount of extracts are applied and extracted by boiling or reflux, filtered, and concentrated under reduced pressure to obtain concentrates.

As disclosed by Korean Pat. Appln. No. 93-9048, the composition for oral cavity is effective to use Taraxacum by itself only, but it is preferable to use a combination of Taraxacum and other plants in aspects of antibiotic and plaque formation inhibiting ability.

The disclosed mixing ratio of plant extracts among the ingredients for oral cavity of the reference is 0.001–10 weight % on the basis of dry-hardened substance, preferably 0.005–5 weight %. If it is mixed with the ratio of below 0.001%, tooth decay or periodontal disease inhibiting effect will be too weak. If it is mixed with the ratio of above 10%, it will not be suitable to be used as the composition for oral cavity because of the original color and bitter taste of the plants' own.

The composition for oral cavity disclosed by Korean Pat. Appln. No. 93-9048 is produced by using appropriate ingredients depending on types of the products. For example, in case of toothpaste ingredients, ingredients included in conventional toothpaste are included, and for these ingredients abrasives such as alumina, silica gel, precipitated silica, Calcium carbonate, Calcium monohydrophosphate and Sodium bicarbonate, humectants such as sorbitol, glycerin and polyethylene glycol, foaming agents such as Sodium lauryl sulfate, Sodium lauryl sarcosinate and Dodecylbenzene sulfonate, binding agents such as carboxymethyl cellulose, Carageenan, Polyacrylate, sweetening agents such as saccharine, aspartame and stevioside, antiseptics such as para-oxy methyl benzoate and para-oxy propyl benzoate, medicine ingredients such as Sodium fluoride, Sodium fluorophosphate, Allantoin, Zinc salt, vitamins, salts, Tranexamic acid, Strontium Chloride and Trichlon, flavors, pigments and pH controller are used. Other compositions for oral cavity may be produced by selecting suitable ingredients depending on types and objectives and then using conventional method with the disclosed plant extracts.

As an example, Korean Pat. Appln. No. 93-9048 discloses a test for testing antibiotic ability of plant extracts. To 30 g of dried and sliced Taraxacum, Lonicera flower, Scutellaria root, Gardenia fruit, Pulsatilla root and Pueraria root, 300 ml of distilled water, ethanol or methanol was applied, extracted by boiling or reflux for 3 hours, and the obtained liquid was filtered with filtering paper, and then centrifuged. This solution was concentrated under reduced pressure, and dried substances shown in Table 1 were obtained.

Separate obtained extracts or mixture of obtained extracts with appropriate concentration was applied to Brain Heart Infusion cultivation paper, streptococcus mutants was inoculated, and cultivated in 37 degrees Celsius for 24 hours. Then the cultivated bacteria were dispersed uniformly with a mixer, and the absorbency ($A_R$) was measured using spectrophotometer (DU series 60 by Beckman, wavelength of 550 nm). Also, one that does not include plant extracts was set to be a control experiment and the absorbency in this case ($A_B$) was measured. Then antibiotic ability and bacteria growth inhibiting ability were compared and estimated. The estimated results are shown in Tables 2 and 3 below.

$$\text{bacteria growth inhibiting rate} = \left(1 - \frac{A_R}{A_B}\right) * 100$$

TABLE 1

The amount of plant extracts obtained (from 30 g)

| Extracting Solvent | Plants | | | | | |
|---|---|---|---|---|---|---|
| | Taraxacum | Gardenia Fruit | Lonicera Flower | Scutellaria Root | Pulsatilla Root | Pueraria Root |
| Ethanol | 3.6 | 6.1 | 4.7 | 8.6 | 6.2 | 5.8 |
| Methanol | 3.2 | 5.5 | 4.3 | 7.6 | 5.6 | 4.9 |

TABLE 2

Bacteria growth inhibiting rate of plant extracts (%)

| | Inhibiting Rate | |
|---|---|---|
| Plants | 250 ppm (methanol) | 250 ppm (ethanol) |
| Taraxacum | 37 | 42 |
| Gardenia fruit | 26 | 31 |
| Lonicera flower | 14 | 11 |
| Scutellaria root | 13 | 14 |
| Pulsatilla root | 12 | 17 |
| Pueraria root | 23 | 20 |

TABLE 3

Bacteria growth inhibiting rate and activating rate of combinations of plant extracts

| Plants | Extracting Solvent (Ethanol) | |
|---|---|---|
| | Inhibiting Rate (%) | Rise Rate (%) |
| Taraxacum + Gardenia fruit | 98 | 24 |
| Gardenia fruit + Lonicera flower | 61 | 19 |
| Gardenia fruit + Scutellaria | 65 | 20 |
| Taraxacum + Pulsatilla root | 81 | 22 |
| Taraxacum + Pueraria root | 86 | 24 |

*Rise rate is a value after subtracting the sum of inhibiting rate % (total concentration: 500 ppm) of ethanol extracts from inhibiting rate % (total concentration: 500 ppm) of combination of plant extracts.

From Table 2 above, it is shown that antibiotic ability of Taraxacum is the best and from Table 3 the combination of Taraxacum extracts and another plant extract shows much better antibiotic ability than Taraxacum extract itself. Thus, it is found that the rise effect is when Taraxacum extract was combined with extracts of Taraxacum, Lonicera flower, Scutellaria root, Gardenia fruit, Pulsatilla root and Pueraria root.

As another example, Korean Pat. Appln. No. 93-9048 discloses an experiment on plaque formation inhibition. Plant extracts obtained by the first example above were mixed in test tube with brain heart infusion cultivation paper whose 2% is a sugar, and streptococcus mutants cultivated beforehand were inoculated. This was cultivated anaerobically in 37 degrees Celsius for 24 hours, and plaque was formed. Plaque and bacteria body in this mixture were dispersed with mixer and supersonic crusher, and the absorbency was measured with spectrophotometer (wavelength of 550). Also, one that does not include plant extracts was set to be a control experiment and the absorbency in this case ($A_B$) was measured. Then antibiotic ability and bacteria growth inhibiting ability were compared and estimated. The estimated results are shown in Table 4 below.

$$\text{plaque formation inhibiting rate} = \left(1 - \frac{A_R}{A_B}\right) * 100$$

TABLE 4

Plaque formation inhibiting rate of plant extracts

| Plant Name | Mixing Ratio | Total Concentration | Extracting Solvent | Inhibiting Rate |
|---|---|---|---|---|
| Taraxacum + Gardenia fruit | 1:2 | 150 | Methanol | 41 |
| | | 300 | Ethanol | 75 |
| Taraxacum + Lonicera | 1:3 | 200 | Ethanol | 52 |
| | | 400 | Ethanol | 84 |
| Taraxacum + Scutellaria | 1:1 | 200 | Ethanol | 35 |
| | | 400 | Ethanol | 68 |

From Table 4 above, the combination of plant extracts has excellent plaque formation inhibiting effect. Also, excellent plaque formation inhibiting effect is shown even with a different mixing ratio.

SUMMARY OF THE INVENTION

Accordingly, it is a principal object of the present invention to overcome the above-mentioned problems encountered to prior arts and to provide a novel herb medicine extract-containing striped dentifrice composition, wherein the transport of colorants at the interface from colored component to the base component decreases markedly with high clearness of the coloured component—accurate color distribution rate of the stripe of the dentifrice components in filling the tube and/or squeezing in use—but the colored component and the base component have almost identical fluidity, and which suppresses the formation of plaque.

As a result of the intensive and thorough research, the present inventors now surprisingly have found that a herb medicine extract-containing striped dentifrice which consists essentially of a colored component comprising herb medicine extracts and a base component can exhibit no bleeding of the coloring materials of the herb medicine extracts at the interface between the colored component and the base component in addition to being more vivid in color, by formulating the colored component almost identically to the base component with particular compositional ingredients.

Based on the finding, the herb medicine extract-containing striped dentifrice composition of the present invention consists essentially of a striped dentifrice component containing herb medicine extracts which suppress the formation of plaque at an amount of 0.001 to 10% by weight on the basis of dry solid substance, and a base dentifrice component, each component comprising the following ingredients at the substantially same amount:

a. 30–60% by weight of an abrasive that has a BET surface area of 10 $m^2/g$ or less and an average particle diameter of 1 to 30 μm upon measuring by Coulter Counter method, and shows oil absorption (linseed oil, ml/100 g) of 50 or less;

b. 0.1 to 10% by weight of a binder selected from the group consisting of xanthan gum, carrageenan, sodium carboxymethylcellulose, and the mixtures thereof;

c. 0.1 to 3.0% by weight of an alkyl sulfate of anionic surfactants; and d. 20 to 70% by weight of a humectant.

DETAILED DESCRIPTION OF THE INVENTION

Extracts from medicinal herbs which are known to be suppressive of the formation of plaque may be contained in the colored dentifrice component, that is, the striped dentifrice component of the composition according to the present invention, the concrete examples of which are described in Korean Pat. Appln. No. 93-9048, Korean Pat. Publication No. 91-1919, Korean Pat. Publication Laid-Open No. 91-18007, Japanese Pat. Publication Laid-Open Nos. Sho 56-83416, Sho 57-58610, Sho 57-58611, Sho 57-58612, Sho 57-58513, Sho 57-56415, Sho 59-152313 and Hei 1-151512, and Japanese Pat. Publication Nos. Hei 3-66283 and Hei 3-32524. Of them, preferred are the materials extracted from taraxacum, gardenia, lonicera, scutellaria, pulsatilla and/or pueraria.

The term "herb medicine extracts" as used in the specification and claim means extracts from medicinal herbs which itself contain pigment or coloring material, or dentally useful ingredients extracted from medicinal herbs and the trace colorants described in the above-cited patents. The herb medicine extracts are preferably contained at an amount of 0.001 to 10% by weight based on the dry solid substance, irrespective of colorant, and more preferably at an amount of 0.005 to 5% by weight.

In the striped dentifrice composition of the present invention, compositional ingredients which are contained at the same amounts in the striped dentifrice component and the base dentifrice component and thus, allow the two dentifrice components to show identical flow property, include an abrasive, a binder, a anionic surfactant, a humectant and other ordinary agents known to those knowledgeable to the art.

An abrasive useful for the composition of the present invention is aluminum hydroxide which has a BET surface area of 10 $M^2/g$ or less with an average particle diameter of 1 to 30 $\mu$m and shows oil absorption of 50 ml or less of linseed oil per 100 g. Preferred is aluminum hydroxide which has a BET surface of 0.2 to 5 $m^2/g$ with an average particle diameter of 5 to 15 $\mu$m and shows oil absorption of 20 to 40 ml of linseed oil per 100 g. Such aluminum hydroxide is commercially available from Showa Denko, Japan, under the tradename "Higilite H 32", or from B.A. Chemicals under the tradename "AF 240", "AF 260" or "AF 280". The abrasive is present at the substantially same amount for each of the striped dentifrice component and the base dentifrice component in the composition of the present invention, and preferably at an amount of 30 to 60% by weight for each dentifrice component, and more preferably at an amount of 40 to 50% by. weight.

Compared with in conventional toothpastes, binder is used at relatively large amounts in the composition of the present invention together with said abrasive, with the aim of preventing the transport of colorant, keeping clear color and distributing the dentifrice components uniformly. While ordinary toothpastes contain 0.5 to 1.5% by weight of binder, each of the striped dentifrice component and the base dentifrice component contains binder at the substantially same amounts ranging from 0.1 to 10% by weight and more preferably from 1.5 to 5% by weight.

Examples of binder useful for the composition of the present invention include polysaccharide gums such as xanthan gum, carrageenan and sodium carboxymothylcellulose. Of them, more preferable binders are xanthan gum and carrageenan.

When using only polysaccharide as a binder, since the total amount of polysaccharide gum is larger in the composition of the present invention than in ordinary toothpastes, causing a problem in formulating dentifrice composition, as the polysaccharide gum is hydrated, and in uniformly squeezing the two dentifrice components out of the toothpaste tube. To avoid this problem, polysaccharide which has a large shear thinning rate and is readily hydrated by virtue of its high dispersibility, is recommended. In this regard, it is preferred that xanthan gum be used solely or in combination with carrageenan.

As a surfactant generally useful for toothpaste compositions, there is exemplified an anionic surfactant such as alkyl sulfoate, monoglyceride sulfoate, α-olefin sulfonate and monoglyceride sulfonate, nonionic surfactant such as polyoxyethylene sorbitan fatty acid ester, polyoxyethylene (cured) castor oil, glycerin fatty acid ester, sorbitan fatty acid ester, saccharose fatty acid ester and alkylol amide, and an amphoteric surfactant such as Fluoronic F-108 and Miranal $C_2M$. For the composition of the present invention, alkyl sulfoate of anionic surfactants is used, including sodium lauryl sulfate. The anionic surfactants are contained in each of the striped dentifrice component and the base dentifrice component at the substantially same amounts ranging from 0.1 to 3.0% by weight and more particularly 0.5 to 2.0% by weight.

In order to present stability and a little viscosity to the composition of the present invention or prevent the composition from being dried upon exposure to the air, humectant is used. Examples of available humectant include glycerin, sorbitol, polyethylene glycol and propylene glycol. The amount of humectant, which may vary according to the particular formulation and toothpaste tube, is present on the order of 20 to 70% by weight for each of the striped dentifrice component and the base dentifrice component in the present invention and preferably on the order of 20 to 50% by weight. Like other ingredients of the present invention, the humectant is contained at the substantially same amount in each of the components.

Besides the above compositional ingredients, the striped dentifrice composition of the present invention may comprise a sweetening agent such as saccharin sodium, aspartam, sorbitol, glycyrrhizic acid, acesulfame and stevioside, a preservative Such as methyl parahydroxy benzoate, propyl parahydroxy benzoate and salicylic acid, and the drug effectors, which are exemplified by sodium fluoride, sodium monofluorophosphate, allantoin, zinc salts, vitamins, salt, tranexamic acid, chlorohexidin salts, enzymes, strontium chloride and trichlosan, perfume and pH controlling agents.

The striped dentifrice composition of the present invention is commercialized by filling it in appropriate tubes such as aluminum tubes, laminate tubes and pump-type tubes by means of a striped dentifrice-filling machine such as a co-extrusion filling machine sold by Norden Pac International AB. 1 to 3 lines of the striped dentifrice may be filled at an amount of 1 to 70% by weight based on the weight of the base dentifrice.

A better understanding of the present invention may be obtained in light of following examples which are set forth to illustrate, but are not to be construed to limit, the present invention.

EXAMPLES I TO IV AND COMPARATIVE EXAMPLES I TO III

Striped toothpastes were formulated as indicated in Tables I and II below.

The herb medicine extracts were obtained by adding 30 g of each of sliced and dried a herb group comprising *Taraxacum platycarpum* H. Dahlstedt, *Gardenia jasminoides* Ellis, *Lonicera japonica* Thunberg, *Scutellaria baicalensis* Georgi, *Pulsatilla koreana* Nakai and *Pueraria thumbergiana* Bentham, in a solvent mixture comprising 300 ml of each of water and methanol or ethanol, shaking or refluxing for 3 hrs. to extract medicinally useful substances, passing the solution through a filtering paper, centrifuging the filtered solution, and concentrating the supernatant in vacuum. The following Table III shows the amounts of the obtained herb medicine extracts on the basis of dry solid substance.

The prepared toothpastes were filled in laminate tubes by use of a co-extrusion filling machine such as that sold by Norden Pac International AB. After being stored for 2 month at 37° C., the toothpastes were tested for the following properties. These results are given as shown in Table IV below.

A. Clearness of colored stripe; Clearness of colored stripe according to time was evaluated when squeezing the toothpastes out of the tubes. The evaluation was expressed numerically. The higher the point is, the better the clearness is.

B. Bleeding of colorant: The bleeding of the colorants from the colored dentifrice component to the base dentifrice component was observed. The degree of the bleeding was evaluated and expressed numerically. The higher the point is, the lower the bleeding of colorant is.

C. Fluidity (Ease of squeezing): The easiness of squeezing a predetermined amount of toothpaste out of tube was evaluated and expressed numerically. The higher the point is, the better the distribution is.

TABLE I

| | Examples | | | | | | | |
|---|---|---|---|---|---|---|---|---|
| | I | | II | | III | | IV | |
| Ingredients | Base | Stripe | Base | Stripe | Base | Stripe | Base | Stripe |
| Aluminum Hydroxide (Surface Area 1.6 m²/g) | 50 | 50 | 50 | 50 | — | — | — | — |
| Aluminum Hydroxide (Surface Area 4.5 m²/g) | — | — | — | — | 50 | 50 | 50 | 50 |
| Abrasive Silica (Surface Area 50 m²/g) | — | — | — | — | — | — | — | — |
| Thickening Silica (Surface Area 190 m²/g) | — | — | — | — | — | — | — | — |
| Light Calcium Carbonate (surface Area 14 m²/g) | — | — | — | — | — | — | — | — |
| Heavy Calcium Carbonate (Surface Area 4.5 m²/g) | — | — | — | — | — | — | — | — |
| Sodium carboxy Methyl Cellulose | — | — | — | — | — | — | — | — |
| Xanthan Gum | 2.0 | 2.0 | 1.0 | 1.0 | 0.5 | 0.5 | 1.5 | 1.5 |
| Carrageenan | — | — | 1.0 | 1.0 | 1.5 | 1.5 | 0.5 | 0.5 |
| SLS | 2.0 | 2.0 | 2.0 | 2.0 | 2.0 | 2.0 | 2.0 | 2.0 |
| Polyoxy ethylene Castor oil | — | — | — | — | — | — | — | — |
| Fluoronic F-108 | — | — | — | — | — | — | — | — |
| MIRANAL C₂M | — | — | — | — | — | — | — | — |
| Taraxacum Extract | — | 0.2 | — | 0.05 | — | — | — | — |
| Scutellaria Extract | — | — | — | 0.1 | — | 0.05 | — | — |
| Lonicera Extract | — | — | — | 0.05 | — | 0.05 | — | — |
| Gardenia Extract | — | 0.1 | — | — | — | — | — | 0.05 |
| Pulsatilla Extract | — | 0.1 | — | — | — | — | — | — |
| Pueraria Extract | — | — | — | — | — | 0.05 | — | 0.05 |
| Sorbitol (70%) | 27 | 27 | 27 | 27 | 27 | 27 | 27 | 27 |
| Saccharine | 0.2 | 0.2 | 0.2 | 0.2 | 0.2 | 0.2 | 0.2 | 0.2 |
| Sodium Mono-fluorophosphate | 0.76 | 0.76 | 0.76 | 0.76 | 0.76 | 0.76 | 0.76 | 0.76 |
| Salt | 2.0 | 2,0 | 2.0 | 2.0 | 2.0 | 2.0 | 2.0 | 2.0 |
| Pigment | — | 0.005 | — | 0.005 | — | 0.005 | — | 0.005 |
| Water to final | 100 | 100 | 100 | 100 | 100 | 100 | 100 | 100 |

TABLE II

| | Comparative Examples | | | | | |
|---|---|---|---|---|---|---|
| | 1 | | 2 | | 3 | |
| Ingredient | Base | Stripe | Base | Stripe | Base | Stripe |
| Aluminum Hydroxide (Surface Area 1.6 m²/g) | — | 50 | — | — | — | — |
| Aluminum Hydroxide (Surface Area 4.5 m²/g) | — | — | — | — | — | — |
| Abrasive Silica (Surface Area 50 m²/g) | 12 | — | 12 | 12 | — | — |
| Thickening Silica (Surface Area 190 m²/g) | 8 | — | 8 | 8 | — | — |
| Light Calcium Carbonate (Surface Area 14 m²/g) | — | — | — | — | 20 | 20 |
| Heavy Calcium Carbonate (Surface Area 4.5 m²/g) | — | — | — | — | 25 | 25 |
| Sodium Carboxy Methyl Cellulose | 0.8 | 1.0 | 0.8 | 0.8 | 0.4 | 0.4 |
| Xanthan Gum | — | — | — | — | — | — |
| Carrageenan | — | — | — | — | 0.4 | 0.4 |
| SLS | 1.0 | 1.0 | 1.0 | 1.0 | 1.0 | 1.0 |
| Polyoxyethylene Castor oil | 1.0 | 1.0 | — | — | — | — |
| Fluoronic F-108 | — | — | — | — | 1.5 | 1.5 |
| MIRANAL C₂M | — | — | 2.0 | 2.0 | — | — |
| Taraxacum Extract | — | 0.2 | — | 0.05 | — | — |
| Scutellaria Extract | — | — | — | 0.1 | — | 0.05 |
| Lonicera Extract | — | — | — | 0.05 | — | 0.05 |
| Gardenis Extract | — | 0.1 | — | — | — | — |
| Pulsatilla Extract | — | 0.1 | — | — | — | — |
| Pueraria Extract | — | — | — | — | — | 0.05 |
| Sorbitol (70%) | 45 | 27 | 45 | 45 | 27 | 27 |
| Saccharine | 0.2 | 0.2 | 0.2 | 0.2 | 0.2 | 0.2 |
| Sodium Mono-fluoro phosphate | 0.76 | 0.76 | 0.76 | 0.76 | 0.76 | 0.76 |
| Salt | 2.0 | 2.0 | 2.0 | 2.0 | 2.0 | 2.0 |
| Pigment | — | 0.005 | — | 0.005 | — | 0.005 |
| Water to final | 100 | 100 | 100 | 100 | 100 | 100 |

TABLE III

| Extracting Solvent | Amount of Extracts from Medicinal Herbs (Unit: g) | | | | | |
|---|---|---|---|---|---|---|
| | Taraxacum | Gardenis | Lonicera | Scutellaria | Pulsatilla | Pueraria |
| Ethanol | 3.8 | 8.1 | 4.7 | 8.6 | 6.2 | 5.8 |
| Methanol | 3.2 | 5.5 | 4.3 | 1.6 | 5.6 | 4.9 |

TABLE IV

| Exam. No | Clearness of Stripe | Bleeding of colorant | Fluidity |
|---|---|---|---|
| Exam. 1 | 4 | 5 | 5 |
| Exam. 2 | 5 | 5 | 5 |
| Exam. 3 | 4 | 4 | 5 |
| Exam. 4 | 5 | 5 | 4 |
| C. 1 | 1 | 1 | 1 |
| C. 2 | 3 | 2 | 2 |
| C. 3 | 3 | 2 | 2 |

As apparent from the Tables above, while the toothpastes of Comparative Examples I to III, wherein the striped dentifrice components are formulated differently from the base dentifrice components, are poor in clearness and fluidity of the striped components and show a strong tendency to bleed to base components, the toothpastes of Example I to IV, wherein the formulations of the striped dentifrice components are substantially the same as those of the base dentifrice components, show little or no bleeding in addition to being far superior in clearness and fluidity.

Other features, advantages and embodiments of the present invention disclosed herein will be readily apparent to those exercising ordinary skill after reading the foregoing disclosures. In this regard, while specific embodiments of the invention have been described in considerable detail, variations and modifications of these embodiments can be effected without departing from the spirit and scope of the invention as described and claimed.

What is claimed is:

1. In a process of formulating a dentifrice composition having a striped dentifrice component and a base dentifrice component, and where the striped dentifrice component contains a coloring that is prevented from bleeding into the base dentifrice component, wherein the improvement comprises:

formulating each of the striped dentifrice component and the base dentifrice component to have the following ingredients at the substantially same amount, whereby the striped dentifrice component and the base dentifrice component have substantially identical fluidity:

a. 30–60% by weight of an abrasive that has a BET surface area of 10 $m^2/g$ or less and an average particle diameter of 1 to 30 $\mu$m upon measurement by Coulter Counter method, and shows oil absorption (linseed oil, ml/100 g) of 50 or less;

b. 0.1 to 10% by weight of a binder selected from the group consisting of xanthan gum, carrageenan, sodium caraboxylmethylcellulose, and the mixtures thereof;

c. 0.1 to 3.0% by weight of an alkyl sulfate of anionic surfactants; and d. 20 to 70% by weight of a humectant;

and formulating the striped dentifrice component to further include herb extracts at an amount of 0.001 to 10% by weight, on the basis of dry solid substance, wherein said herb extracts contain coloring material and come from the group consisting of *Taraxacum platycarpum* H. Dahlstedt, *Gardenis jasminoides* Ellis, *Lonicera japonica* Thunberg, *Scultellaria baicallensis* Georgi, *Pulsatilla koreana* Nakai, *Pueraria thunbergiana* Bentham and the combinations thereof.

2. A herb extract-containing non-bleeding striped dentifice composition produced by the process of claim 1.

3. The improved process in accordance with claim 1, wherein said abrasive is aluminum hydroxide ($Al(OH)_3$).

4. The improved process in accordance with claim 1, wherein said binder comprises xanthan gum solely or in combination with carrageenan.

5. The improved process in accordance with claim 1, wherein said anionic surfactant is sodium lauryl sulfate.

* * * * *